(12) United States Patent
Benetti et al.

(10) Patent No.: US 12,171,526 B2
(45) Date of Patent: Dec. 24, 2024

(54) CLEANING APPLIANCE

(71) Applicant: Dyson Technology Limited, Wiltshire (GB)

(72) Inventors: Michele Benetti, Bristol (GB); Nikita Shmidt, Swindon (GB)

(73) Assignee: Dyson Technology Limited, Wiltshire (GB)

( * ) Notice: Subject to any disclaimer, the term of this patent is extended or adjusted under 35 U.S.C. 154(b) by 364 days.

(21) Appl. No.: 17/790,342

(22) PCT Filed: Nov. 16, 2020

(86) PCT No.: PCT/GB2020/052922
§ 371 (c)(1),
(2) Date: Jun. 30, 2022

(87) PCT Pub. No.: WO2021/148764
PCT Pub. Date: Jul. 29, 2021

(65) Prior Publication Data
US 2023/0024733 A1    Jan. 26, 2023

(30) Foreign Application Priority Data
Jan. 20, 2020  (GB) ..................... 2000804

(51) Int. Cl.
*A61B 5/00*   (2006.01)
*A46B 11/00*  (2006.01)
(Continued)

(52) U.S. Cl.
CPC ........ *A61B 5/0088* (2013.01); *A46B 15/0036* (2013.01); *A61B 5/0077* (2013.01);
(Continued)

(58) Field of Classification Search
CPC ... A61B 5/0088; A61B 5/0036; A61B 5/0077; A61C 17/28; A46B 2200/1046;
(Continued)

(56) References Cited

U.S. PATENT DOCUMENTS 8,186,997 B2    5/2012  Binner et al.
11,426,264 B2 *  8/2022  Serval .................. G06V 40/166
(Continued)

FOREIGN PATENT DOCUMENTS

CN    103188966 A    7/2013
CN    103764063 A    4/2014
(Continued)

OTHER PUBLICATIONS

Office Action received for Chinese Patent Application No. 202080093972.3, mailed on Feb. 16, 2023, 12 pages (6 pages of English Translation and 6 pages of Original Document).
(Continued)

*Primary Examiner* — David J Walczak
(74) *Attorney, Agent, or Firm* — Tucker Ellis LLP; Michael G. Craig (57) ABSTRACT

A dental treatment appliance transmits a pulsed light signal towards the oral cavity and captures images of the oral cavity from light returned from the oral cavity. A controller actuates the treatment of the oral cavity of the user depending on the captured images.

15 Claims, 8 Drawing Sheets

(51) Int. Cl.
*A46B 13/02* (2006.01)
*A46B 13/04* (2006.01)
*A46B 15/00* (2006.01)
*A61C 17/28* (2006.01)

(52) U.S. Cl.
CPC ............ *A61C 17/28* (2013.01); *A46B 11/002* (2013.01); *A46B 13/02* (2013.01); *A46B 13/04* (2013.01); *A46B 2200/1066* (2013.01)

(58) Field of Classification Search
CPC ..... A46B 11/00; A46B 11/001; A46B 11/002; A46B 11/0062; A46B 11/0072; A46B 13/008; A46B 13/02; A46B 13/04
USPC ................................. 401/268, 270, 280–282
See application file for complete search history.

(56) References Cited

U.S. PATENT DOCUMENTS

| 2010/0309302 A1 | 12/2010 | Yang |
| 2011/0232012 A1 | 9/2011 | Nanda |
| 2014/0199651 A1 | 7/2014 | Adachi |
| 2018/0168332 A1 | 6/2018 | Wagner et al. |
| 2022/0096220 A1* | 3/2022 | Jeng ........................ A61C 17/26 |

FOREIGN PATENT DOCUMENTS

| CN | 204744476 U | 11/2015 |
| JP | 2015-186131 A | 10/2015 |
| JP | 2016-058838 A | 4/2016 |
| JP | 2016-533804 A | 11/2016 |
| JP | 2018-019730 A | 2/2018 |
| WO | 2019/072018 A1 | 4/2019 |

OTHER PUBLICATIONS

Office Action received for Japanese Patent Application No. 2022-543777, mailed on Sep. 5, 2023, 6 pages (3 pages of English Translation and 3 pages of Original Document).

Search Report for GB Patent Application No. 2000804.1, Issued on Jul. 6, 2020, 1 page.

* cited by examiner

CLEANING APPLIANCE

CROSS-REFERENCE TO PRIOR APPLICATION

This application is a § 371 National Stage Application of PCT International Application No. PCT/GB2020/052922 filed Nov. 16, 2020, which claims the priority of United Kingdom Application No. 2000804.1, filed Jan. 20, 2020, each of which are herein incorporated by reference in their entirety.

FIELD OF THE INVENTION

The present invention relates to a treatment appliance. The treatment appliance is preferably a handheld treatment appliance, and is preferably a surface treating appliance. In preferred embodiments of the invention, the appliance is a dental treatment appliance. In a preferred embodiment, the appliance is an electric toothbrush having a fluid delivery system for delivering a fluid to the oral cavity of the user. This fluid may be toothpaste, or a fluid for improved interproximal cleaning. Alternatively, the appliance may not include any bristles or other elements for brushing teeth, and may be in the form of a dedicated oral treatment appliance.

BACKGROUND OF THE INVENTION

Electric toothbrushes generally comprise a tool which is connected to a handle. The tool comprises a stem and a brush head bearing bristles for brushing teeth. The brush head comprises a static section which is connected to the stem, and at least one moveable section which is moveable relative to the static section, for example with one of a reciprocating, oscillating, vibrating, pivoting or rotating motion, to impart a brushing movement to bristles mounted thereon. The stem houses a drive shaft which couples with a transmission unit within the handle. The transmission unit is in turn connected to a motor, which is driven by a battery housed within the handle. The drive shaft and the transmission unit convert rotary or vibratory motion of the motor into the desired movement of the moveable section of the brush head relative to the static section of the brush head.

It is known to incorporate into an electric toothbrush a fluid delivery system for generating a burst of working fluid for interproximal cleaning. For example, WO2016/185154 describes a toothbrush having a handle, a brush head and stem extending between the brush head and the handle. The brush head includes a nozzle from which working fluid is delivered to the oral cavity of the user, and a brush unit which moves relative to the nozzle to brush a user's teeth. The nozzle is moveable relative to the handle as the appliance is moved along the user's teeth. The toothbrush is operable in a selected one of two different modes. In a first mode, the user depresses a button to actuate the delivery of working fluid from the nozzle. In a second mode, a controller actuates the delivery of working fluid to the nozzle automatically depending on a signal received from a sensor. The sensor is located in the handle of the toothbrush. A pivoting arm located within the stem connects the nozzle to a magnet located adjacent to the sensor and which moves relative to the sensor as the nozzle moves relative to the handle, for example as the nozzle moves into, or out from, an interproximal gap in the user's teeth.

SUMMARY OF THE INVENTION

In a first aspect, the present invention provides a dental treatment appliance comprising:

a handle;
an optical system comprising illuminating means for illuminating an oral cavity of a user, and image capturing means for capturing an image of the illuminated oral cavity;
a dental treatment system for delivering a treatment to the oral cavity; and
moving means for moving the illuminating means relative to the handle;
wherein the moving means is configured to move the illuminating means relative to the handle at a first frequency F1, and the illuminating means is configured to illuminate the oral cavity at a second frequency F2 to generate a plurality of illumination events each second.

Unlike the appliance described in WO2016/185154, the treatment of the oral cavity of the user is actuated in dependence on one or more of the features contained in the captured image of the oral cavity. For example, the captured image may include a region of plaque in the oral cavity, an interproximal region between adjacent teeth of the oral cavity or a gum line separating teeth from gum. The dental treatment system preferably comprises a controller which determines from the captured image whether treatment of the oral cavity is required, for example, using neural network models stored in its memory. The treatment of the oral cavity may be actuated by the controller and may comprise, for example, the ejection of fluid into the interproximal region to remove matter located therein, the removal of plaque from the teeth of the user, or the irrigation of the gum line, as appropriate.

During a treatment of the oral cavity, the illuminating means of the optical system is moved relative to the handle. The illuminating means may be moved along a path of any desired shape relative to the handle. In a preferred embodiment, the moving means is arranged to move the illuminating means reciprocally relative to the handle, preferably along a curved path, more preferably along an arcuate path. The moving means is preferably arranged to move the illuminating means relative to the handle along a path which is arranged substantially perpendicular to a longitudinal axis of the handle. In a preferred embodiment, the illuminating means is reciprocally swept about the longitudinal axis of the handle by an angle in the range from 10 to 30°, preferably at a frequency F1 in the range from 200 to 300 Hz. In a preferred embodiment, the frequency F1 of the oscillation of the illuminating means is 250 Hz.

The illuminating means preferably comprises one or more light emitting diodes (LEDs). The illuminating means is preferably selected to emit visible light, more preferably selected to emit white light, preferably having a colour temperature in the range of 3,000 to 7,000K.

The optical system comprises a window for receiving light from the oral cavity, and from which light is conveyed to the image capturing means. The window of the optical system is preferably arranged to move with the illuminating means. The window is preferably located adjacent to the LEDs. The LEDs may be arranged about the window. The window may be in the form of a flat transparent panel, formed from glass or a plastics material, or it may be in the form of a curved transparent member so as to provide a lens of the optical system.

The image capturing means may be arranged to move with the illuminating means relative to the handle. For example, the appliance may comprise a stem extending between a head and a handle, and the image capturing means may be located in either the stem or the head of the appliance so as to move with the illuminating means and the window relative to the handle. Alternatively, the image capturing means may be located in the handle, with light being conveyed from the window to the image capturing means through the stem of the appliance.

The image capturing means is preferably configured to capture a number N of images, or frames, per second. For example, the image capturing means may be arranged to capture 20 to 30 images, or frames per second, with an exposure time per frame in the range from 30 to 40 msec. If the oral cavity were to be illuminated continuously, the movement of the illuminating means relative to the handle at a frequency in the range from 200 to 300 Hz during image capture would result in the generation of a blurred image. Such an image can be detrimental to the accuracy with which a controller can identify features such as plaque or an interproximal gap within the captured image, and so be detrimental to the accuracy of the treatment of the oral cavity by the appliance.

Through pulsing the illumination of the optical cavity at a frequency F2, we have found that the sharpness of the captured image can be improved in comparison to a situation where the oral cavity is illuminated continuously by the illuminating means, which can improve the accuracy of the treatment of the oral cavity.

The illuminating means may be activated once per oscillation cycle. In other words, the illuminating means may be configured to illuminate the optical cavity at a frequency F2, where F2=F1. In one embodiment, the illuminating means illuminates the optical cavity at a frequency F2 of 250 Hz, and so there are 250 pulsed illuminations of the oral cavity, or "illumination events", each second. The illuminating means is preferably activated at the aforementioned reference position.

The intensity or the duration of each illumination event may be varied depending on the ambient light intensity. For example, the appliance may comprise a sensor for measuring the ambient light intensity, and wherein a controller may be arranged to vary at least one of the intensity and the duration of each illumination event depending on the measured ambient light intensity, for example, so that the intensity of the illumination of the oral cavity is relatively constant.

The moving means is preferably arranged to move the illuminating means towards and away from at least one reference position. For example, where the illuminating means is moved in a reciprocally sweeping movement along a curved path, a reference position may be located at the centre of that path. Alternatively, or additionally, reference positions may be located midway between the centre and the extremities of that path.

The image capturing means may be in the form of a global shutter camera, in which all of the pixels of the sensor of the camera are exposed simultaneously and for the same period of time during the time taken to capture an image, for example 25 msec when the camera is operating at an image capture rate of 40 frames per second. However, in a preferred embodiment the image capturing means is in the form of a rolling shutter camera, in which the sensor of the camera is exposed in a progressive manner to capture an image. As is known, the sensor is divided into a number of rows and columns of pixels. During image capture, each row (or column) of pixels is exposed for the same period of time, and within each row all of the pixels are exposed for the same period of time. In this type of camera, exposure of the rows of pixels is sequential, in that the instant at which exposure starts and ends is slightly different for each row.

Banding effects are formed by alternating groups of dark and light rows of pixels. We have found that the bands stay in the same position during the acquisition of a sequence of images if the frequency F2 is an integer multiple of the frame rate of the camera. To inhibit the formation of banding effects in the captured image of the oral cavity, each row of pixels is preferably exposed to the same number of illumination events. The start time at which each row of pixels are exposed is preferably selected so that each row of pixels is exposed to the same number of illumination events to inhibit banding.

In a second aspect, the present invention provides a dental treatment appliance comprising:
  a handle;
  an optical system comprising illuminating means for illuminating an oral cavity of a user, and image capturing means for capturing an image of the illuminated oral cavity;
  a dental treatment system for delivering a treatment to the oral cavity; and
  moving means for moving the illuminating means relative to the handle;
  wherein the moving means is configured to move the illuminating means relative to the handle at a first frequency F1, and the illuminating means is configured to illuminate the oral cavity at a second frequency F2 to generate a plurality of illumination events each second, and wherein the image capturing means comprises a rolling shutter camera having a sensor comprising a plurality of rows of pixels, the rows of pixels being exposed sequentially, and wherein each row of pixels is exposed to the same number of illumination events.

When the user holds the handle of the appliance at a fixed position relative to the oral cavity, the images captured by the camera appears stationary with time when the frequency F2 of the illumination of the optical cavity is the same as the frequency F1 of the movement of the illuminating means relative to the handle. Depending on the distance between the camera and teeth being imaged by the optical system, this can result in a relatively narrow field of view of the camera, which, depending on the position of the appliance within the oral cavity, could prevent some treatable features of the oral cavity from being captured.

As an alternative to synchronizing the illumination of the oral cavity with the movement of the illuminating means, the appliance may be configured such that the frequency F2 of the illumination of the optical cavity is different from the frequency F1 of the movement of the illuminating means relative to the handle. By desynchronizing the illumination of the optical cavity from the movement of the illuminating means, the image captured by the camera can appear to move, in slow motion, relative to the handle, and thus relative to the oral cavity, even when the user holds the handle of the appliance at a fixed position relative to the oral cavity. This can increase the effective field of view of the camera, and so increases the likelihood that any treatable feature within the oral cavity will be detected from the images captured by the camera.

The frequency F2 is preferably selected such that $0<|F1-nF2|<N$, where N is the number of images captured per second by the image capturing means, and n is a positive integer selected such that $|F1-nF2|$ has a minimum value. For example, where F1=250 Hz and N=25 frames per second, with n=1 F2 may be selected from values between 225 and 275 Hz.

In a third aspect, the present invention provides a dental treatment appliance comprising:
a handle;
an optical system comprising illuminating means for illuminating an oral cavity of a user, and image capturing means for capturing an image of the illuminated oral cavity;
a dental treatment system for delivering a treatment to the oral cavity; and
moving means for moving the illuminating means relative to the handle;
wherein the moving means is configured to move the illuminating means relative to the handle at a first frequency F1, and the illuminating means is configured to illuminate the oral cavity at a second frequency F2 selected such that $0<|F1-nF2|<N$, where N is the number of images captured per second by the image capturing means, and n is a positive integer selected such that $|F1-nF2|$ has a minimum value.

The appliance may be in the form of an appliance for treating an oral condition of the user. For example, the appliance may be in the form of a dedicated interproximal cleaning appliance for cleaning between the gaps in the user's teeth. The treatment system may comprise a fluid delivery system for delivering working fluid to the oral cavity of the user. Depending on the image captured by the optical system, the treatment system actuates the delivery of working fluid to the oral cavity to dislodge matter located within a gap between the user's teeth. The movement of the illuminating means relative to the handle can enable such a gap to be detected in advance of the fluid delivery system being located in an optimal position for delivering working fluid into the gap. This can enable the fluid delivery system to be "primed" by the controller of the treatment system, for example by drawing fluid from a fluid reservoir into a fluid chamber of a pump, once the gap has been detected so that fluid delivery system is ready to deliver working fluid into the gap once it is optimally positioned to do so. This can minimise the length of time that the fluid delivery system is held in a primed position in comparison, for example, to an arrangement in which the fluid delivery system is primed immediately after working fluid has been expelled from the fluid chamber of the pump, which could result in the fluid delivery system remaining in a primed position if no further gaps are detected before the appliance is switched off.

In this case, the moving means may be arranged to move the illuminating means relative to a nozzle for delivering working fluid to the oral cavity. The nozzle preferably extends along a nozzle axis, which passes through a fluid outlet located at the tip of the nozzle. The nozzle axis may be aligned generally orthogonal to the longitudinal axis of the handle. The moving means may comprise a drive mechanism for driving the movement of the illuminating means relative to the nozzle. The drive mechanism preferably comprises a transmission unit connected to the illuminating means, and a drive unit for driving the transmission unit to move the illuminating means relative to the nozzle. The drive unit is preferably located in the handle, and preferably comprises a motor. The transmission unit may comprise a drive shaft extending between the motor and the illuminating means. The drive shaft may be housed within a stem which extends between the handle and the illuminating means. The stem may form part of a cleaning tool which is detachably connected to the handle. The nozzle may be mounted on the stem so that the illuminating means moves relative to the nozzle.

Alternatively, the appliance may be in the form of a toothbrush which has the additional function of improved interproximal cleaning through the emission of working fluid into the interproximal gap. Where the appliance is in the form of a toothbrush, the cleaning tool, or stem, preferably comprises a plurality of bristles. The bristles are preferably arranged around the nozzle, and may be arranged circumferentially about the nozzle. A plurality of bristles may be attached to a static section of the cleaning tool, which section is not moveable relative to the handle. Alternatively, or additionally, a plurality of bristles may be attached to a moveable section of the cleaning tool, which section is moveable relative to the handle.

In a preferred embodiment, the appliance comprises a brush unit comprising a bristle carrier and a plurality of bristles mounted on the bristle carrier, with the bristle carrier being moveable relative to the handle. The bristle carrier is preferably located on the head of the appliance. The appliance comprises a drive mechanism for driving the movement of the bristle carrier relative to the handle. The drive mechanism preferably comprises a transmission unit connected to the bristle carrier, and a drive unit for driving the transmission unit to move the bristle carrier relative to the handle. The drive unit is preferably located in the handle.

The drive mechanism is preferably arranged to drive the movement of the illuminating means relative to the handle. The illuminating means is thus preferably arranged to move with the bristle carrier relative to the handle. The illuminating means may be arranged to move relative to the handle with the same movement pattern as, or with a different movement pattern from, the bristle carrier. For example, the illuminating means, the window and the bristle carrier may be arranged to move reciprocally in a sweeping movement relative to the handle. The illuminating means and the window may be spaced from the bristle carrier, or at least one of the illuminating means and the window may be mounted on the bristle carrier. For example, the drive mechanism may be arranged to move the stem relative to the handle so as to move the brush unit, the illuminating means and the window simultaneously relative to the handle.

The nozzle is preferably arranged to move with the illuminating means relative to the handle. For example, the illuminating means and the nozzle may be mounted on or adjacent to the bristle carrier so that the drive mechanism moves the bristle carrier, the nozzle, the illuminating means and the window simultaneously relative to the handle.

The illuminating means and the window are preferably arranged proximate to the nozzle so that region of the oral cavity towards which the signal is transmitted is substantially the same as the region which is subsequently treated by the treatment system. The illuminating means and the nozzle may be positioned side by side on the cleaning tool.

The controller is preferably located in the handle of the appliance. Whilst signals may be transmitted wirelessly between the optical system and the controller, it is preferred that signals are transmitted between the optical system and the controller along a physical transmission path located within the appliance. Preferably, the transmission path extends along part of the drive mechanism. This can allow the number of components of the appliance to be minimised.

As mentioned above, the drive mechanism is preferably located in the handle, and preferably comprises a transmission unit connected to the bristle carrier, and a drive unit for driving the transmission unit to move the bristle carrier relative to the handle. The transmission unit is preferably in the form of a shaft which is moved relative to the handle by the motor. The frequency of the vibration of the shaft is preferably in the range from 200 to 300 Hz. The motor preferably extends about the shaft so that the shaft rotates or vibrates relative to the handle upon excitation of the motor. The stem of the cleaning tool is mounted on the shaft.

The transmission path preferably extends along the transmission unit, more preferably along an external surface of the shaft. For example, a conductive track for conveying signals towards the controller may be formed on the external surface of the shaft. The track is preferably connected to a handle contact for engaging a cleaning tool contact when the cleaning tool is attached to the handle. The handle contact is preferably an annular contact which extends about an end part of the shaft. The cleaning tool preferably comprises a recess for receiving this part of the shaft to connect the cleaning tool to the handle. The cleaning tool contact is preferably located within the recess, and preferably protrudes inwardly from an internal peripheral surface of the recess to engage the handle contact when the cleaning tool is attached to the handle. A wire, track or other conductive member extends between the cleaning tool contact and the detecting means to convey signals from the detecting means to the cleaning tool contact.

In addition to extending along part of the transmission unit, the transmission path preferably also extends along part of the drive unit. The drive unit preferably comprises means for engaging the shaft, and the engaging means is preferably arranged to convey signals towards the controller. The drive unit is preferably arranged to move, more preferably rotate, the shaft away from an equilibrium position to move the cleaning tool relative to the handle against the force of the engaging means. The engaging means is arranged to urge the shaft back towards its equilibrium position when the driving force of the drive unit is removed. The engaging means may comprise a spring member, and in a preferred embodiment comprises a torsion spring. A wire, track or other conductive member extends between the spring member and the controller to convey signals from the spring member to the controller.

As mentioned above, the dental treatment system preferably comprises a fluid delivery system for delivering a working fluid to the oral cavity of the user. The fluid delivery system preferably comprises a fluid reservoir and a pump, with the controller being arranged to actuate the pump to draw working fluid from the fluid reservoir and eject working fluid towards the nozzle. The controller is preferably arranged to actuate the pump to eject a burst of working fluid towards the nozzle. The volume of each burst of working fluid which is generated by the fluid delivery system is preferably less than 1 ml, more preferably less than 0.5 ml. In a preferred embodiment, the volume of the burst of working fluid generated by the fluid delivery system is in the range from 0.05 to 0.4 ml. The fluid delivery system is preferably configured to deliver a burst of working fluid to the nozzle at a static pressure in the range from 3 to 10 bar.

The transmission unit preferably defines part of the fluid delivery system. The shaft preferably comprises a bore which defines part of the fluid delivery system.

The appliance preferably comprises a user interface for enabling a user to select a mode of operation of the appliance before the commencement of a treatment process. The user interface may be located on the handle of the appliance, and preferably comprises at least one user operable switch or button. The user interface may comprise a display located on the handle for displaying information about a chosen operating mode. Alternatively, the appliance may be connected wirelessly to a remote device having a display for displaying that information. The remote device may be in the form of a dedicated display or a personal device. The remote device may also include a user interface, such as a touch sensitive display, for enabling a user to select an operating mode for the appliance.

Features described above in connection with the first aspect of the invention are equally applicable to the second or third aspect of the invention, and vice versa.

BRIEF DESCRIPTION OF THE DRAWINGS

Preferred features of the invention will now be described, by way of example only, with reference to the accompanying drawings, in which.

DETAILED DESCRIPTION OF THE INVENTION

Figure 1A:
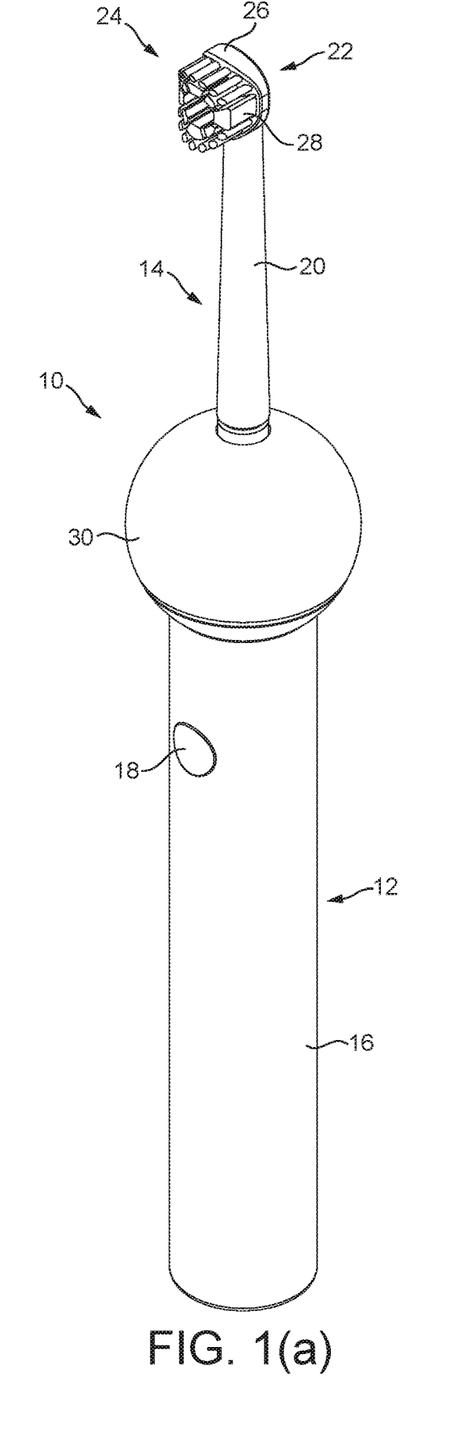
FIG. 1(a) is a perspective view, from the front, of a dental cleaning appliance.
Figure 1B:
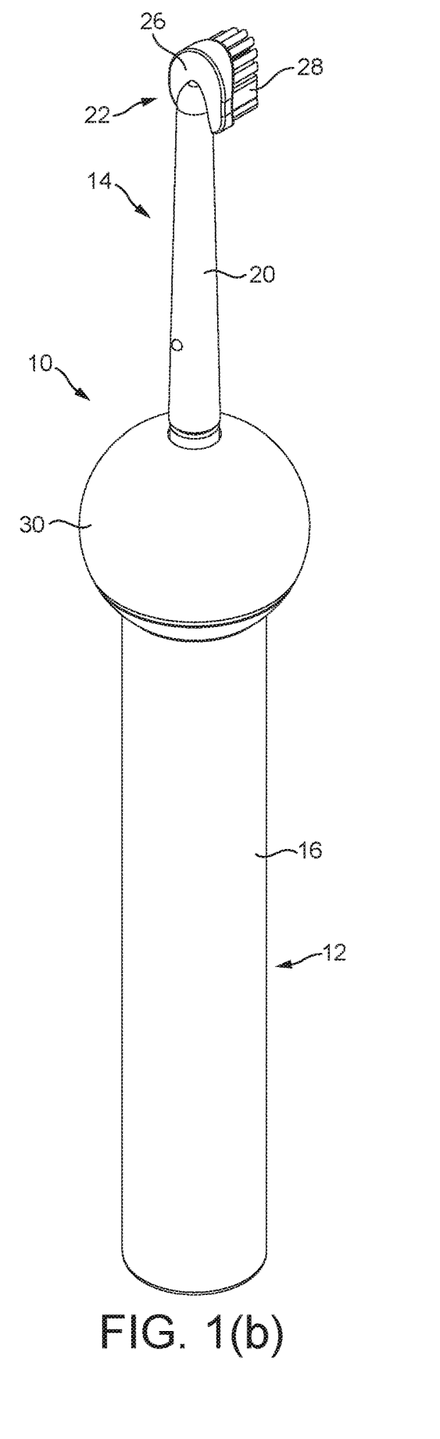
FIG. 1(b) is a perspective view, from the rear, of the appliance of FIG. 1(a)

FIGS. 1(a) and 1(b) illustrate external views of an embodiment of a dental cleaning appliance 10. In this embodiment, the appliance is in the form of a handheld appliance, which is in the form of an electric toothbrush having an integrated assembly for dispensing a working fluid for improved interproximal cleaning.

The appliance 10 comprises a handle 12 and a cleaning tool 14. The handle 12 comprises an external body 16 which is preferably formed from plastics material. The body 16 is generally cylindrical in shape. The handle 12 comprises a user interface. The user interface comprises a user operable button 18 which is located within an aperture formed in the body 16 so as to be depressible by the thumb of a hand which is gripping the body 16 of the handle 12. Optionally, the handle 12 may comprise a display which is positioned so as to be visible to a user during use of the appliance. The appliance 10 may be connectable to a remote display, such as a display of a personal device or mobile telephone, to enable the user to select operating modes or parameters for the appliance 10 using the button 18 and/or the remote display, as described in more detail below.

The cleaning tool 14 comprises a stem 20 and a head 22. The stem 20 is elongate in shape, which serves to space the head 22 from the handle 12 to facilitate user operability of the appliance 10. In this embodiment, the head 22 of the cleaning tool 14 comprises a brush unit 24, which comprises a bristle carrier 26 and a plurality of sets of bristles 28 mounted on the bristle carrier 26. In this embodiment, the brush unit 24 is rigidly connected to the stem 20. However, in other embodiments the cleaning tool 14 may be provided without a brush unit 24 so that the appliance is in the form of a dedicated oral treatment appliance, for example for cleaning between the gaps in the user's teeth, or for delivering a cleaning or whitening medium to the teeth of the user. In other embodiments, the brush unit 24 may be replaceable.

Figure 2A:
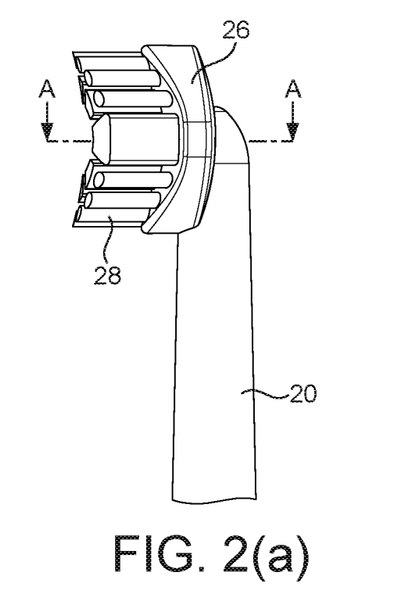
FIG. 2(a) is a side view of a brush unit of the appliance of FIG. 1(a)
Figure 2B:
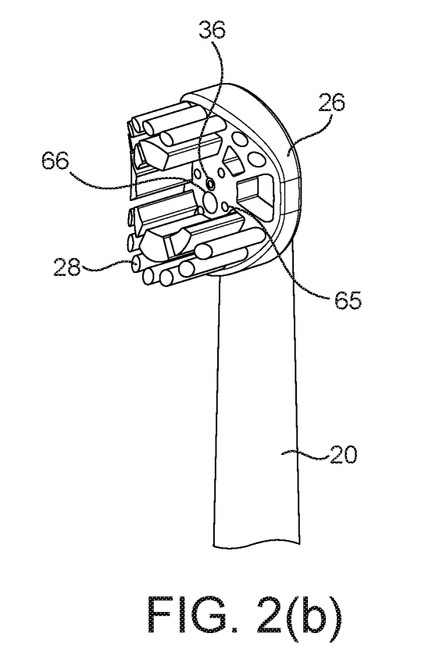
FIG. 2(b) is a perspective view of the brush unit with some of the bristles omitted to reveal a sensor and nozzle of the brush unit.
Figure 2C:
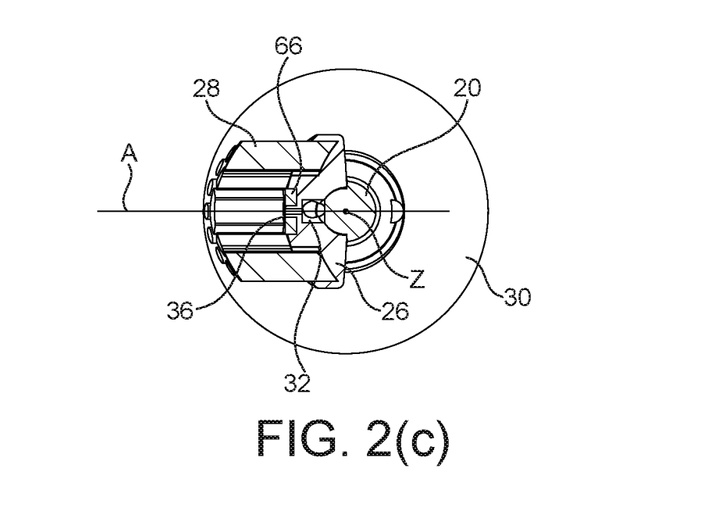
FIG. 2(c) is a sectional view taken along line A-A in FIG. 2(a)

The appliance 10 includes a dental treatment system for delivering a treatment to the oral cavity. In this embodiment, the dental treatment system is arranged to deliver a burst of working fluid to the oral cavity to dislodge matter located in an interproximal gap. However, the dental treatment system may be configured to deliver a whitening fluid, or to remove plaque from the teeth of the user. The dental treatment system may also be configured to deliver a burst of working fluid to the gum line to treat inflammations or infections of the gums, such as gingivitis. With reference also to FIGS. 2(a) to 2(c), the cleaning tool 14 also comprises a fluid reservoir 30 for storing a working fluid, and a nozzle 32 for delivering working fluid to the oral cavity of the user during use of the appliance 10. The working fluid is preferably a liquid working fluid, and in this embodiment is water. The fluid reservoir 32 is mounted on the handle 12 so as to extend about an end of the handle 12. The nozzle 32 is mounted on the head 22 of the cleaning tool 14. In this embodiment which includes a brush unit 24, the bristles 28 are arranged at least partially around the nozzle 32. The nozzle 32 extends along a nozzle axis A, illustrated in FIG. 2(c), which is substantially perpendicular to a longitudinal axis Z of the handle 12.

The nozzle 32 forms part of a fluid delivery system 34 for receiving working fluid from the fluid reservoir 30 and for delivering bursts of working fluid to the oral cavity of a user during use of the appliance 10. Each burst of working fluid preferably has a volume which is less than 1 ml, more preferably less than 0.5 ml. The fluid delivery system 34 is illustrated schematically in FIG. 3. In overview, the tip of the nozzle 32 comprises a fluid outlet 36 through which a burst of working fluid is delivered to the oral cavity of the user. The fluid delivery system 34 comprises a fluid inlet 36 for receiving working fluid from the fluid reservoir 30. In this embodiment, the working fluid is a liquid working fluid, which is preferably water. The fluid inlet 36 is positioned on the handle 12, preferably on the end of the body 16 of the handle 12, and is arranged to connect to a fluid port of the fluid reservoir 30 when the fluid reservoir 30 is connected to the handle 12. As described below, the cleaning tool 14 is detachable from the handle 12, and the fluid reservoir 30 can be pulled away from the handle 12 for replenishment once the cleaning tool 14 has been detached from the handle 12.

Figure 3:
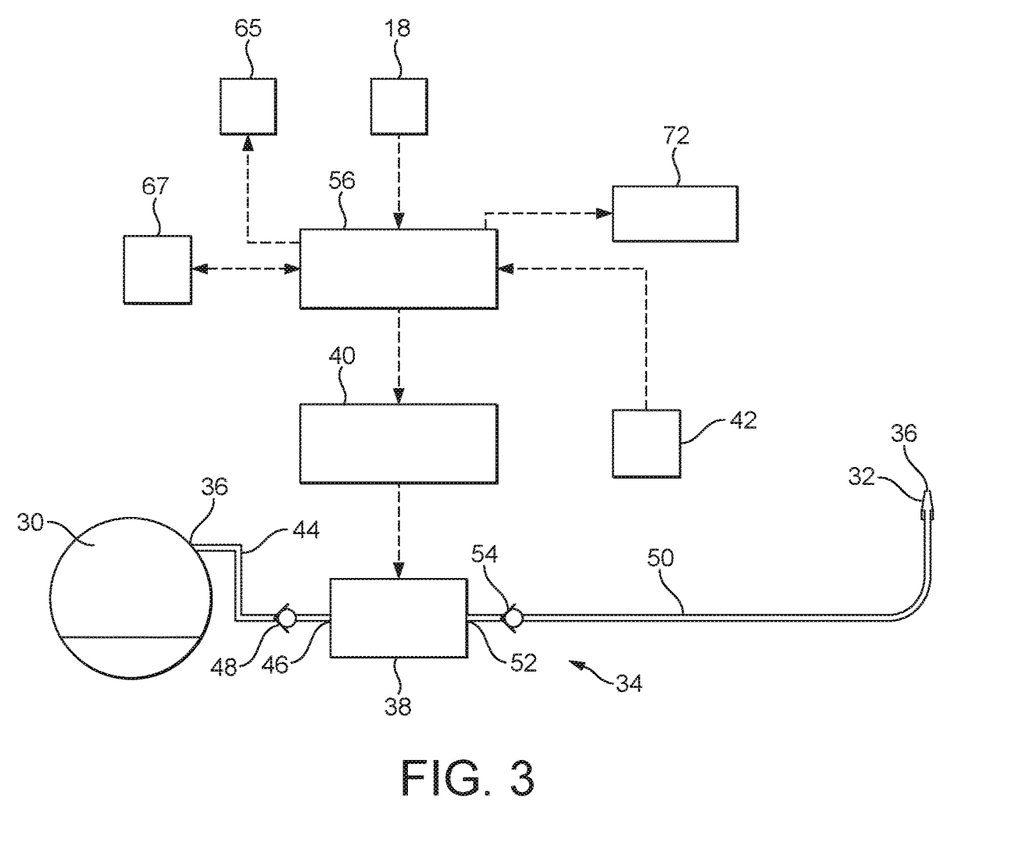
FIG. 3 is a schematic illustration of a fluid delivery system of the appliance.
Figures 4A, 4B:
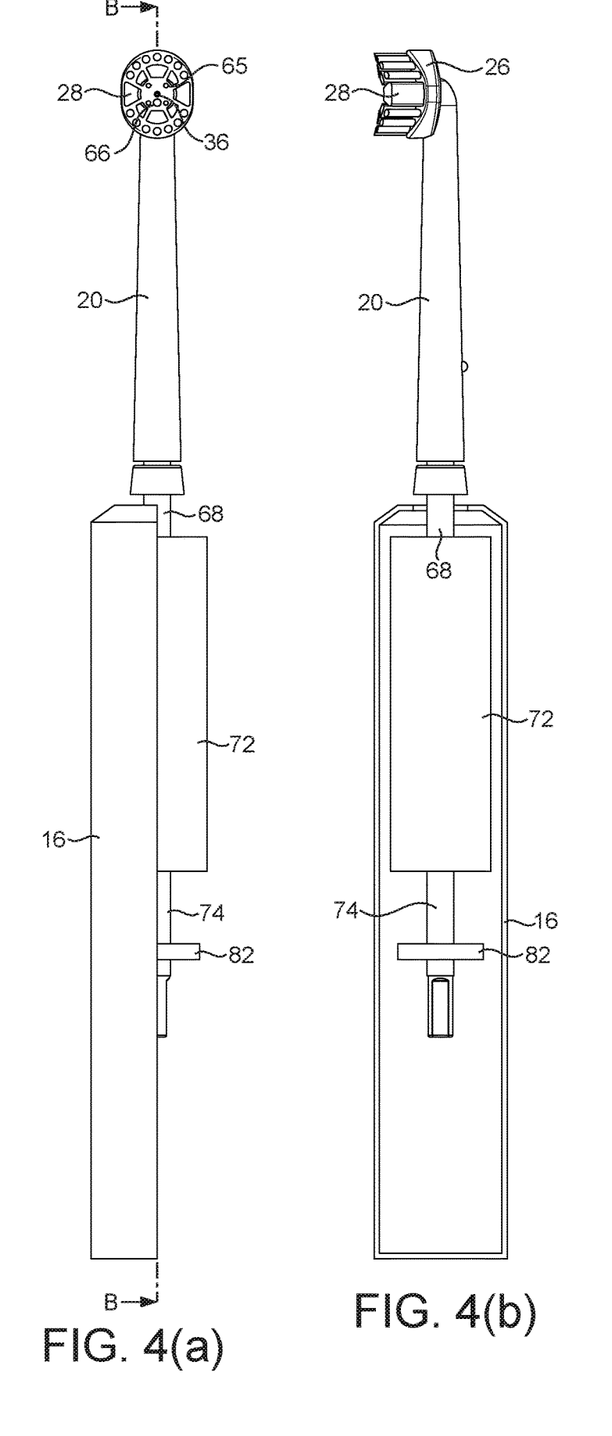
FIG. 4(a) is a front view of part of the appliance of FIG. 1(a), with the fluid reservoir and part of the handle removed.
FIG. 4(b) is a side view of the part of the appliance of FIG. 4(a) and FIG. 4(c) is a perspective view, from above, of the part of the appliance of FIG. 4(a)
Figure 4C:
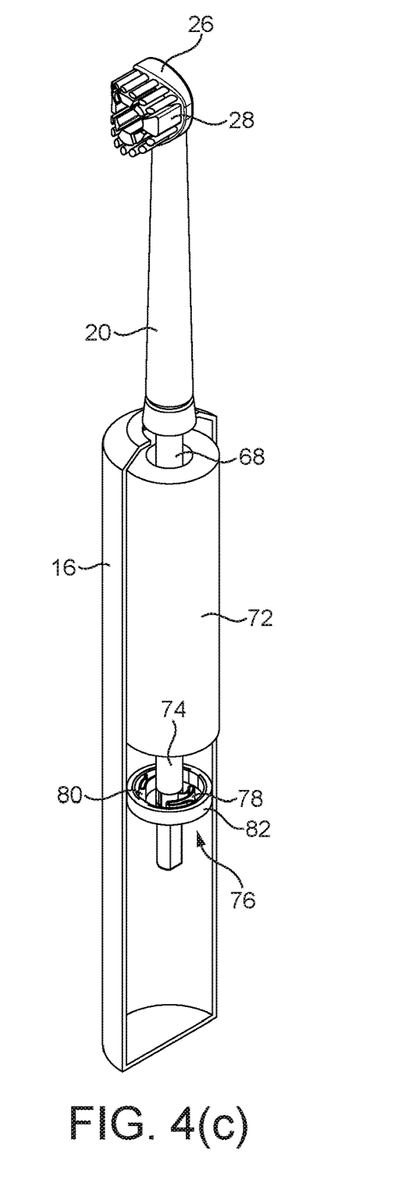

The fluid delivery system 34 comprises a pump assembly for drawing working fluid from the fluid reservoir 30 through the fluid inlet 36, and for delivering a burst of working fluid to the nozzle 32. The pump assembly is located within the body 16 of the handle 12, and comprises a positive displacement pump 38 and a drive for driving the pump 38. The drive preferably comprises a pump motor 40. A battery 42 for supplying power to the pump motor 40 is also located in the handle 12. The battery 42 is preferably a rechargeable battery.

A first conduit 44 connects the fluid inlet 36 of the fluid delivery system 34 to a fluid inlet 46 of the pump 38. A first one-way valve 48 is located between the fluid inlet 36 and the pump 38 to prevent water from returning to the fluid reservoir 30 from the pump 38. A second conduit 50 connects a fluid outlet 52 of the pump 38 to the nozzle 32. A second one-way valve 54 is located between the pump 38 and the nozzle 32 to prevent water from returning to the pump 38. A control circuit 56 controls the actuation of the pump motor 40, and so the pump motor 40 and the control circuit 56 provide a drive for driving the pump 38. The battery 42 supplies power to the control circuit 56. The control circuit 56 includes a motor controller which supplies power to the pump motor 40.

The control circuit 56 receives signals generated when the user depresses the button 18 of the user interface. The control circuit 56 may transmit signals to, and receive signals from, a remote device, such as a display or a personal device. In this embodiment, the control circuit 56 also transmits signals to, and receives signals from, an optical system. With reference to FIGS. 2(b) and 2(c), at least part of the optical system is mounted on the head 22 of the appliance 10, and preferably on the bristle carrier 26 of the brush unit 24. In this embodiment, the nozzle 32 is also mounted on the bristle carrier 26 of the brush unit 24. The optical system comprises a plurality of LEDs 65 for illuminating the oral cavity, and a window 66 for receiving light from the oral cavity. The received light is conveyed to a camera 67 for capturing images of the illuminated oral cavity. The window 66 is positioned on the head 22 so that it is located adjacent to the nozzle 32. In this embodiment, the window 66 is located beneath the nozzle 32, and the LEDs 65 are arranged about the window 66. The camera 67 may be located in the head 22 of the appliance 10 so as to minimize the length of the optical path between the window 66 and the camera 67. Alternatively, the camera 67 may be located in the handle 12, and light is conveyed from the window 66 to the camera 67 via imaging optics located between the window 66 and the camera 67. The images generated by the camera 67 are transmitted to the control circuit 56. In dependence on one or more features of the images, the control circuit 56 actuates the pump assembly to deliver one or more bursts of working fluid to the oral cavity. For example, the images generated by the camera 67 can indicate the presence of plaque or an interproximal gap, or a gum line, in response to which the control circuit can activate the dental treatment system to treat the oral cavity.

The cleaning tool 14 is detachably connected to the handle 12. With reference also to FIGS. 4(a) to 6, the handle 12 comprises a male connector, preferably in the form of a spigot 68, which is received by a complementary female connector, preferably in the form of a recessed connector 70, of the stem 20 of the cleaning tool 14. The spigot 68 protrudes outwardly from the end of the handle 12, and preferably in a direction which is parallel to, and more preferably collinear with, a longitudinal axis Z of the handle 12.

The appliance 10 comprises a drive mechanism for driving the movement of the stem 20, and thus the bristle carrier 26, relative to the handle 12. With reference to FIGS. 4(a) to 7, the drive mechanism comprises a transmission unit and a drive unit for driving the transmission unit to move the stem 20 relative to the handle 12. The drive unit comprises a drive motor 72 which is located within the body 16 of the handle 12. The control circuit 56 includes a motor controller which supplies power to the drive motor 72. The button 18 may also be used to activate and deactivate the drive motor 72, for example by depressing the button 18 a predefined number of times within a preset time period, to start, and subsequently stop, a cleaning session. Alternatively, a separate button (not shown) may be provided for activating and deactivating the drive motor 72.

Figure 5:
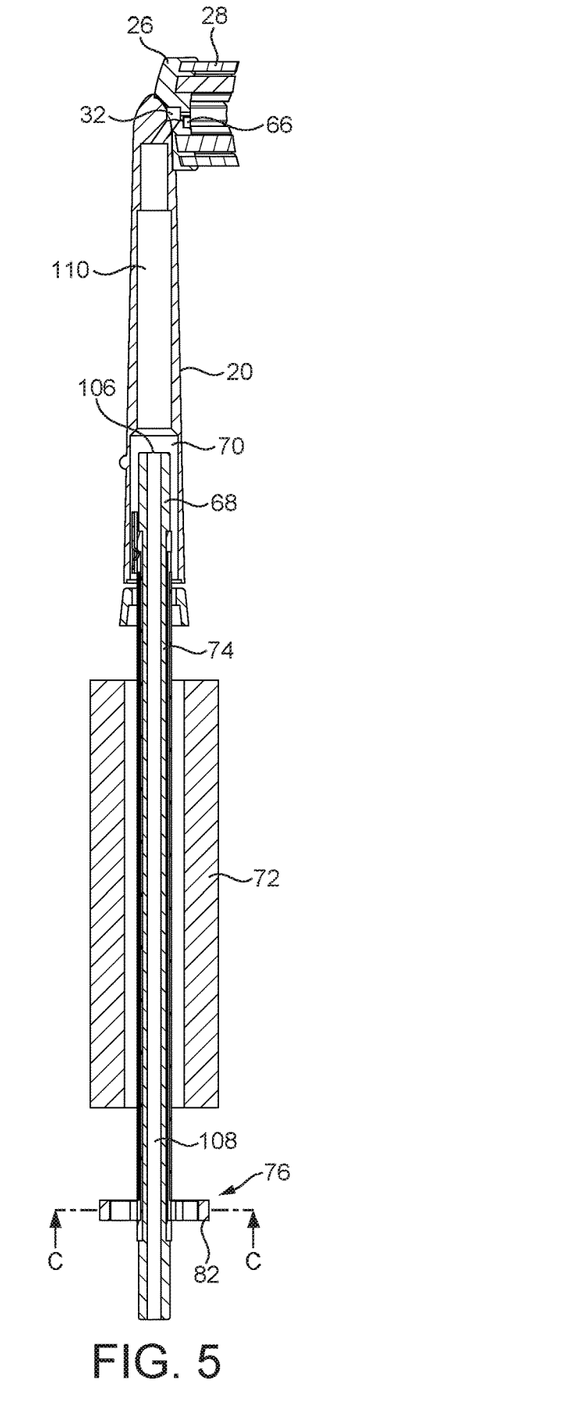
FIG. 5 is a sectional view taken along line B-B in FIG. 4(a)
Figure 6:
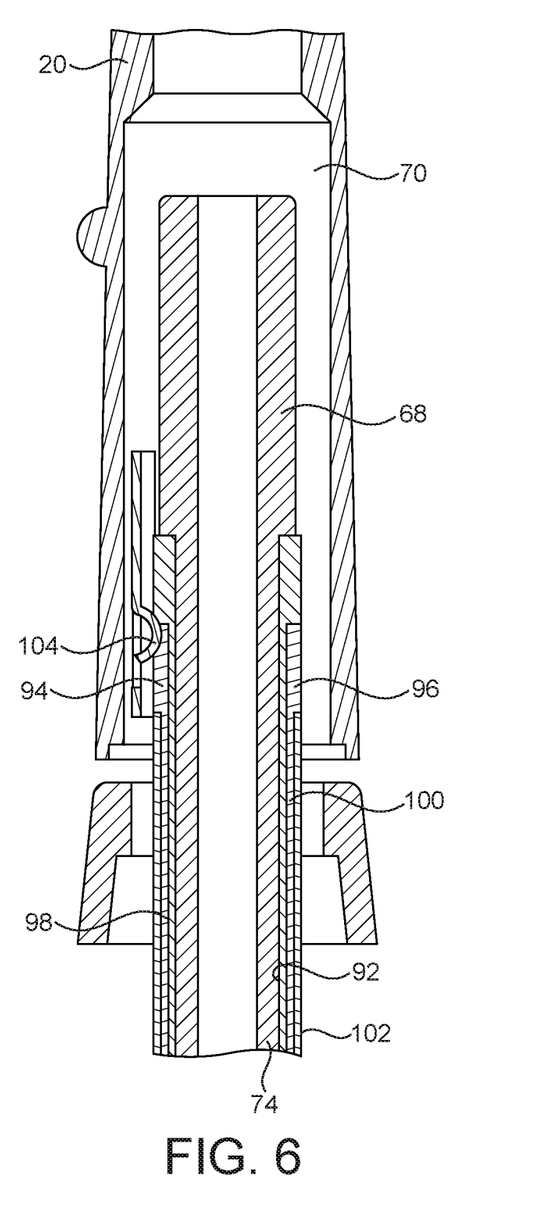
FIG. 6 is a close up of part of FIG. 5.
Figure 7:
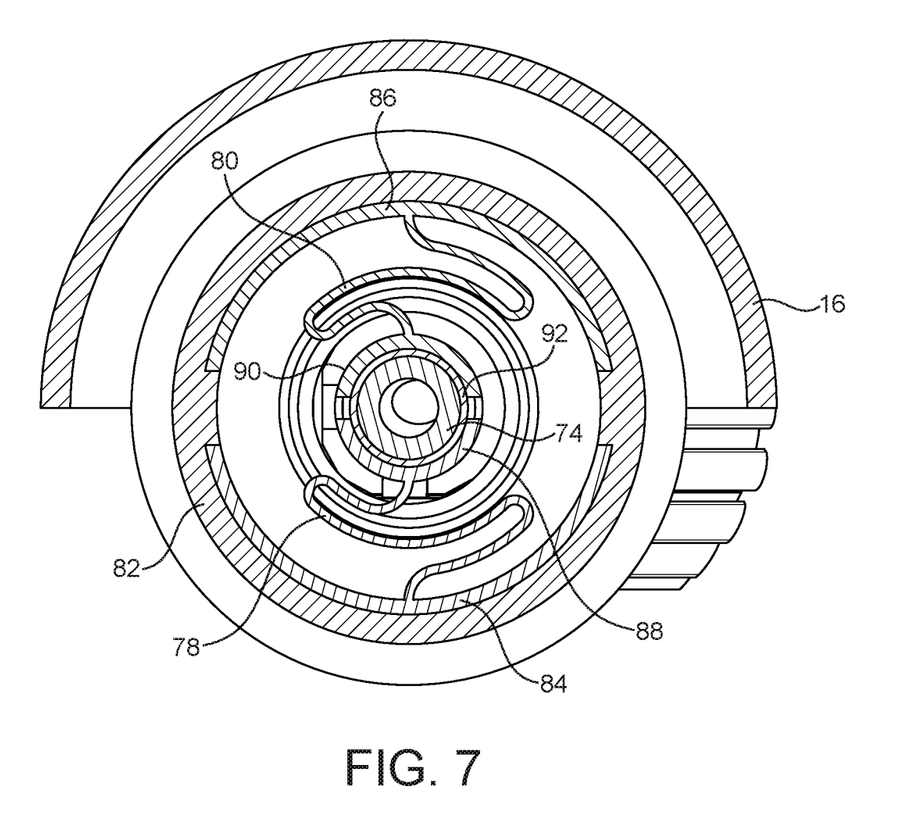
FIG. 7 is a sectional view taken along line C-C in FIG. 5.

The transmission unit comprises a shaft 74 which is driven by the drive unit to oscillate relative to the handle 12. The spigot 68 is connected to, and is preferably integral with, the shaft 74. The drive unit is preferably arranged to oscillate the shaft 74 so that it oscillates about the longitudinal axis Z of the handle 12, preferably at a first frequency F1 in the range from 200 to 300 Hz. In this embodiment, frequency F1 is 250 Hz. The drive motor 72 is arranged to rotate the shaft 74 about the longitudinal axis away from a central position by an angle α. The angle α is preferably in the range from 5 to 15°, and in this embodiment is 5°. The drive unit may further comprise a spring member 76 for engaging the drive shaft 74 to return the shaft 74 to its central position. The spring member 76 comprises a pair of torsion springs 78, 80 located on opposite sides of the drive shaft 74, and each having a first end which engages the drive shaft 74 and a second end which is attached to a support ring 82 which is connected to, or otherwise held in a fixed position relative to, the handle 12.

With reference to FIGS. 8(a) to 8(c), this movement of the shaft 74 relative to the handle 12 causes the bristle carrier 26, and thus the nozzle 32 and the part of the optical system mounted on the bristle carrier 26, to move back and forth along a respective curved paths. With reference to FIG. 8(a), in this embodiment, the bristle carrier 26 is moved about the longitudinal axis Z of the handle 12 between a first angular position, indicated at R in FIG. 8(a) and a second angular position, indicated at L in FIG. 8(a), which are each angularly spaced from a central reference position, indicated at M in FIG. 8(a), by the angle α. The movement of the bristle carrier 26 relative to the handle 12 can be represented as a sinusoidal wave S, illustrated in FIG. 8(b), in which the bristle carrier 26 is at the position M when time t=0, t2, t4, t6, etc., at the position R when t=t1, t5, etc., and at the position L when t=t3, t7, etc.

During use of the appliance 10, drive signals are transmitted from the control circuit 56 to the LEDs 65 to actuate the illumination of the oral cavity by the optical system. Light signals, indicative of the light subsequently returned to the window 66 by reflection from the oral cavity, are conveyed from the window 66 to the camera 67. The camera 67 generates images of the oral cavity from the received light signals, and transmits the generated images to the control circuit 56, in dependence on which the control circuit 56 actuates the delivery of working fluid from the nozzle 32.

The control circuit 56 is located in the body 16 of the handle 12, whilst at least the LEDs 65 of the optical system are located on the brush carrier 26 of the cleaning tool 14. In this embodiment, transmission paths for electrical signals transmitted between the control circuit 56 and the optical system extend along the drive unit. With reference to FIGS. 6 and 7, the second end of each torsion spring 78, 80 is connected to a respective circuit contact 84, 86 formed on the support ring 82. Wires (not shown) extend from each circuit contact 84, 86 to the control circuit 56. The first end of each torsion spring 78, 80 is connected to a respective shaft contact 88, 90 formed on the shaft 74. A first insulating sleeve 92 is located between the shaft 74 and the shaft contacts 88, 90 to electrically insulate the shaft contacts 88, 90 from the shaft 74. Each shaft contact 88, 90 is connected to a respective handle contact 94, 96 by a conductive track 98, 100 which extends along the first insulating sleeve 92. Each handle contact 94, 96 is located on the spigot 68. A second insulating sleeve 102 is located over the conductive tracks 98, 100 so that only the various different electrical contacts of the handle 12 are exposed along the transmission paths. The recessed connector 70 of the cleaning tool 14 includes a pair of cleaning tool contacts (one of which is indicated at 104 in FIG. 6) for engaging a respective handle contact 94, 96 when the cleaning tool 14 is attached to the handle 12. Each cleaning tool contact 104 protrudes inwardly from the internal peripheral surface of the recessed connector 70, and the contacts 104 are connected by wires to the LEDs 65 and, where the camera 67 is located in the brush head 26, to the camera 67.

The second conduit 50, which connects the pump 38 to the nozzle 32, comprises a handle conduit section located within the handle 12, and a cleaning tool conduit section located within the cleaning tool 14. The handle conduit section extends from the fluid outlet 52 of the pump 38 to a handle fluid outlet 106 located at the end of the spigot 68. The handle conduit section comprises an outlet section 108 which is defined by the bore of the shaft 74. The cleaning tool conduit section comprises a conduit (not shown) which extends within the bore 110 of the stem 22 to the nozzle 32.

To operate the appliance 10, the user switches on the appliance 10 by depressing button 18, the action of which is detected by the control circuit 56. Before commencement of a treatment process using the appliance 10, the user can select, using the button 18, the remote display, or a combination of the button 18 and the remote display, an operating mode of the appliance 10. In this embodiment, the appliance 10 has a first operating mode and a second operating mode.

In the first operating mode, the drive mechanism moves the bristle carrier 26 relative to the handle 12. In this mode, the control circuit 56 does not actuate the LEDs 65 to illuminate the oral cavity, and so there is no automatic delivery of working fluid to the oral cavity of the user based on images captured by the optical system. During this first operating mode, the user may actuate the delivery of a single burst of working fluid from the nozzle 32 by depressing the button 18 for less than a preset period of time. This period of time is preferably in the range from 0.5 to 2 sec, and in this embodiment is 1 sec. In response to this depression of the button 18, the control circuit 56 activates the pump 38 to urge a volume of water from a fluid chamber of the pump 38 to the nozzle 32, and to replenish the fluid chamber through drawing a volume of water from the fluid reservoir 30.

In the second operating mode, in addition to the functionality of the first operating mode the control circuit 56 actuates the LEDs 65 to transmit light signals away from the bristle carrier 26, and so towards the oral cavity of the user. Light signals returned by the oral cavity are received by the window 66, and conveyed to the camera 67. The camera 67 may be in the form of a global shutter camera, in which all of the pixels of the sensor of the camera are exposed simultaneously and for the same period of time, for example, 30 to 40 msec, to capture an image. The camera 67 may thus capture around 25 to 30 images per second. However, in this embodiment the camera 67 is in the form of a rolling shutter camera, in which the sensor of the camera 67 is exposed in a progressive manner to capture an image. The sensor is divided into a number of rows and columns of pixels. During image capture, each row (or column) of pixels is exposed for the same period of time, and within each row all of the pixels are exposed for the same period of time. In this embodiment, where the camera 67 captures 25 images, or frames, per second, the illumination of each row of pixels is staggered so that the rows of pixels are exposed sequentially over a period of around 40 msec.

Consequently, during formation of a single image, several oscillations of the bristle carrier 26, and thus the LEDs 65 and the window 66, are conducted. If the LEDs 65 were to be illuminated continuously during image capture, this would result in the generation of a blurred image of the oral cavity, from which it would be difficult for the control circuit 56 to identify features of the oral cavity which require treatment.

Figure 8:
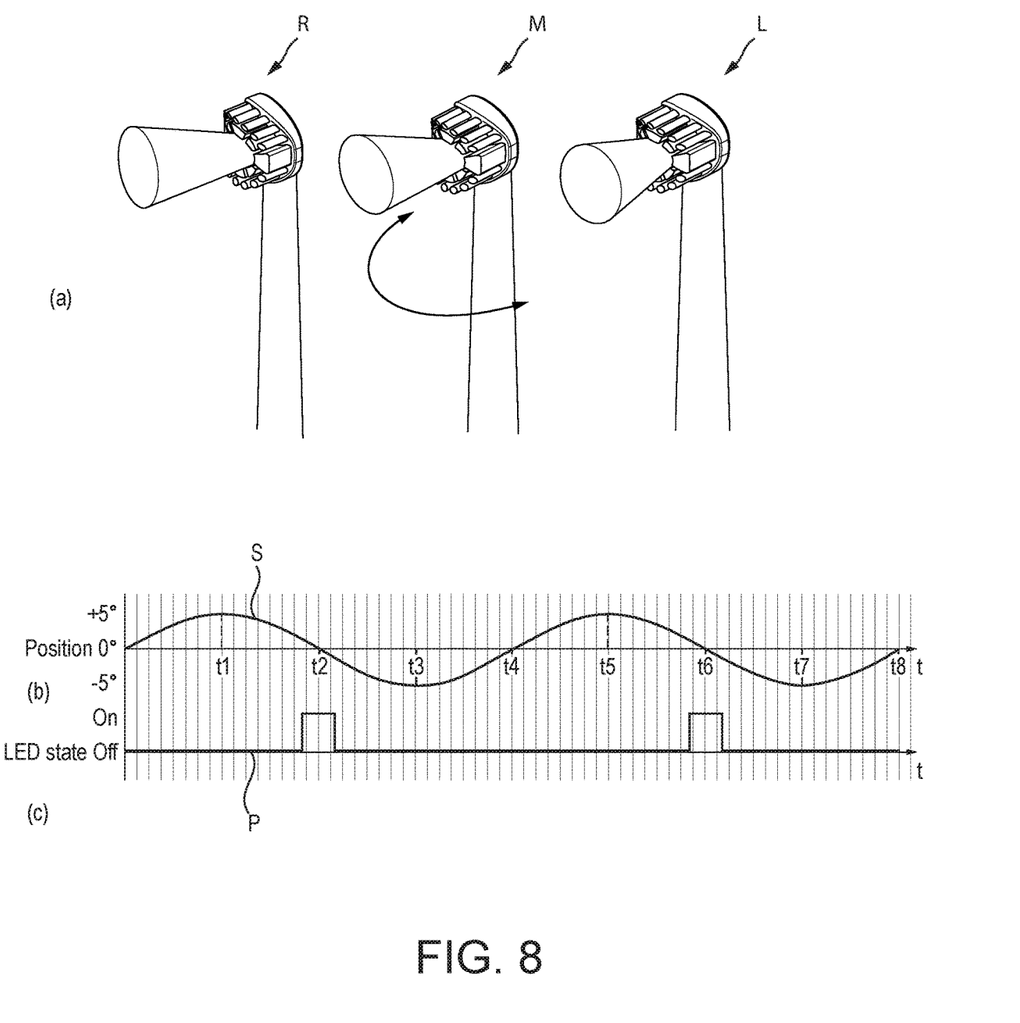
FIG. 8(a) illustrates the field of view of a camera of an optical system of the appliance when at different angular position relative to the handle.
FIG. 8(b) illustrates the angular movement of the camera as a sine wave.
FIG. 8(c) illustrates synchronisation of pulsing of LEDs of the optical system at the zero crossing of the sine wave.

In view of this, the control circuit 56 is arranged to actuate the LEDs 65 to illuminate the oral cavity at a second frequency F2 to generate a plurality of illumination events each second. In a first example, the frequency F2 is the same as F1, which in this embodiment is 250 Hz. As illustrated by trace P in FIG. 8(*c*), the LEDs 65 are activated when the bristle carrier 26 is in the position M, and so at time t=t2, t6, etc. Consequently, allowing for ambient light levels, the vast majority of the light captured by the optical system is generated when the bristle carrier 26, and thus when the LEDs 65 and window 66, are in a single position relative to the handle 12. Allowing for slight movement of the handle 12 relative to the oral cavity during image capture, this has the effect of a relatively static image of the oral cavity being captured by the optical system.

The images captured by the camera 67 are transmitted to the control circuit 56, which determines from the captured image whether treatment of the oral cavity is required, for example through comparing the captured image with images stored in its memory. For example, the control circuit 56 may actuate treatment of the oral cavity when it is determined from a captured image that the nozzle 32 is positioned so as to eject a burst of working fluid into an interproximal gap. When treatment is required, the control circuit 56 is arranged to actuate the treatment of the oral cavity by the fluid treatment system 34 in the same manner as when the button 18 is depressed by the user during the first operating mode. As the images of the oral cavity are captured when the bristle carrier 26 is in the position M, the control circuit 56 is preferably arranged to actuate the treatment of the oral cavity so that the ejection of a burst of working fluid from the nozzle 32 occurs when the bristle carrier 26 is in the position M, that is, in the same position as when the image of the oral cavity was captured by the optical system, so as to optimise the remove of debris or other matter from the gap.

In a second example, the control circuit 56 is arranged to actuate the LEDs 65 to illuminate the oral cavity at a second frequency F2 which is different from the first frequency F1 at which the bristle carrier 26 moves relative to the handle 12, and which is preferably given by the equation 0<|F1−nF2|<N, where N is the number of images captured per second by the camera 67, and n is a positive integer selected such that |F1−nF2| has a minimum value. For example, where F1=250 Hz and N=25 frames per second, with n=1 F2 may be selected from values between 225 and 275 Hz. By desynchronizing the illumination of the optical cavity from the movement of the LEDs 65, the image captured by the camera 67 can appear to move, in slow motion, relative to the handle 12, and thus relative to the oral cavity, even when the user holds the handle 12 of the appliance 10 at a fixed position relative to the oral cavity. This can increase the effective field of view of the camera 67, and so increase the likelihood that any treatable feature within the oral cavity will be detected from the images captured by the camera 67.

In each of the above examples, during exposure of a row of pixels of the sensor the oral cavity is illuminated at the second frequency F2 to generate a plurality of "illumination events" each second, which, in the specific examples provided above, may be in the range from 225 to 275 illumination events per second. This means that during exposure of a row of pixels of the sensor of the camera 67 to the light received from the oral cavity, which camera is arranged to capture 25 frames per second, each row of pixels is exposed to a plurality of illumination events. As any variation in the number of illumination events to which adjacent rows of pixels are exposed could lead to the formation of bands across the captured image, the camera 67 is preferably arranged such that each row of pixels is exposed to the same number of illumination events. This may be achieved through selection of the start time of the exposure of each row of pixels, or through selection of the duration of the period of exposure of each row of pixels, so that every row of pixels is exposed to the same number of illumination events.

The invention claimed is:

1. A dental treatment appliance comprising:
   a handle;
   an optical system comprising illuminating means for illuminating an oral cavity of a user, and a window for receiving light from the illuminated oral cavity, and from which the received light is conveyed to image capturing means for capturing images of the illuminated oral cavity;
   a dental treatment system for delivering a treatment to the oral cavity in dependence on one or more features contained in the captured images; and
   moving means for moving the illuminating means and the window relative to the handle;
   wherein the moving means is configured to move the illuminating means and the window relative to the handle at a first frequency F1, and the illuminating means is configured to illuminate the oral cavity at a second frequency F2 to generate a plurality of illumination events each second.

2. The appliance according to claim 1, wherein the illuminating means comprises a plurality of LEDs.

3. The appliance according to claim 1, wherein the window is located adjacent to the illuminating means.

4. The appliance according to claim 1, comprising a head, and a stem extending between the head and the handle, and wherein the moving means is arranged to move the stem and the head relative to the handle.

5. The appliance according to claim 4, wherein the illuminating means and the window are located on the head of the appliance.

6. The appliance according to claim 4, wherein the head of the appliance comprises a plurality of bristles.

7. The appliance according to claim 1, wherein the dental treatment system comprises a nozzle for ejecting working fluid towards the oral cavity.

8. The appliance according to claim 7, comprising a head, and a stem extending between the head and the handle, and wherein the nozzle is located on the head of the appliance.

9. The appliance according to claim 1, wherein the image capturing means comprises a rolling shutter camera.

10. The appliance according to claim 9, wherein the camera comprises a sensor comprising a plurality of rows of pixels, the rows of pixels being exposed sequentially, and wherein each row of pixels is exposed to the same number of illumination events.

11. The appliance according to claim 1, wherein F1=F2.

12. The appliance according to claim 1, wherein the second frequency F2 is selected such that 0<|F1−nF2|<N, where N is the number of images captured per second by the image capturing means, and n is a positive integer selected such that |F1−nF2| has a minimum value.

13. The appliance according to claim 1, comprising a sensor for measuring the ambient light intensity, and a controller arranged to vary at least one of the intensity and the duration of each illumination event depending on the measured ambient light intensity.

14. The appliance according to claim 1, wherein the moving means is arranged to move the illuminating means and the window relative to the handle along a path which is arranged perpendicular to a longitudinal axis of the handle.

15. The appliance according to claim 14, wherein the moving means is arranged to move the illuminating means and the window relative to the handle reciprocally along a curved, or arcuate, path.

* * * * *